(12) United States Patent
Lugovkin et al.

(10) Patent No.: US 12,091,143 B2
(45) Date of Patent: Sep. 17, 2024

(54) INDIVIDUAL SELF-CONTAINED BREATHING APPARATUS OF CLOSED CYCLE FOR UNDERWATER SUBMERGENCE

(71) Applicant: "AQUABREATHER" LLC, Moscow (RU)

(72) Inventors: Vadim Vladimirovich Lugovkin, St. Petersburg (RU); Maxim Vitalievich Godionenko, St. Petersburg (RU)

(73) Assignee: "AQUABREATHER" LLC, Moscow (RU)

( * ) Notice: Subject to any disclaimer, the term of this patent is extended or adjusted under 35 U.S.C. 154(b) by 715 days.

(21) Appl. No.: 17/278,091

(22) PCT Filed: Dec. 3, 2019

(86) PCT No.: PCT/RU2019/000881
§ 371 (c)(1),
(2) Date: Mar. 19, 2021

(87) PCT Pub. No.: WO2020/139140
PCT Pub. Date: Jul. 2, 2020

(65) Prior Publication Data
US 2021/0347455 A1    Nov. 11, 2021

(30) Foreign Application Priority Data
Dec. 14, 2018    (RU) .......................... RU2018144425

(51) Int. Cl.
*B63C 11/24*    (2006.01)
*A62D 9/00*    (2006.01)
(Continued)

(52) U.S. Cl.
CPC ................ *B63C 11/24* (2013.01); *A62D 9/00* (2013.01); *B63C 11/14* (2013.01); *G01N 33/004* (2013.01)

(58) Field of Classification Search
CPC ......... B63C 11/00; B63C 11/02; B63C 11/12; B63C 11/18; B63C 11/22; B63C 11/24
See application file for complete search history.

(56) References Cited

U.S. PATENT DOCUMENTS 4,266,539 A * 5/1981 Parker ...................... A62B 7/00
                                                                  55/DIG. 35
4,314,566 A * 2/1982 Kiwak ................... B63C 11/24
                                                                    62/51.1
(Continued)

FOREIGN PATENT DOCUMENTS

| CN | 206107521 U | 4/2017 |
| RU | 2155700 C2 | 9/2000 |

(Continued)

*Primary Examiner* — Colin W Stuart
(74) *Attorney, Agent, or Firm* — MUNCY, GEISSLER, OLDS & LOWE, PC

(57) ABSTRACT

An individual self-contained breathing apparatuses of closed cycle is proposed, including an air system, including a compensatory cylinder with compressed gas, a reducer and a manometer; a gas analyzing system; a regenerative device including reactors with cartridges with oxygen regenerating agent; a breathing circuit including a face mask, a space under the face mask, a breathing bag, a valve for releasing pressure in the breathing circuit; connecting air ducts for connecting the breathing circuit to the regenerative system and the air system, whereas all components are positioned in monoblock housing. The apparatus includes no supply of the breathing mixture. The apparatus can be used for recreational diving, technical diving, professional diving or rescue purposes.

11 Claims, 2 Drawing Sheets

(51) Int. Cl.
  *B63C 11/14* (2006.01)
  *G01N 33/00* (2006.01)

(56) References Cited

U.S. PATENT DOCUMENTS

| | | | | |
|---|---|---|---|---|
| 4,423,723 A * | 1/1984 | Winkler | ............... | A62B 9/006 |
| | | | | 128/204.22 |
| 4,450,837 A * | 5/1984 | Ream | ............... | B63C 11/24 |
| | | | | 128/201.27 |
| 4,567,889 A | 2/1986 | Lehmann | | |
| 4,939,647 A * | 7/1990 | Clough | ............... | B63C 11/24 |
| | | | | 128/204.22 |
| 5,036,841 A | 8/1991 | Hamilton | | |
| 5,072,728 A | 12/1991 | Pasternack | | |
| 2011/0041848 A1* | 2/2011 | Stone | ............... | B63C 11/12 |
| | | | | 128/203.14 |
| 2011/0297153 A1* | 12/2011 | Grimsey | ............... | B63C 11/24 |
| | | | | 128/204.18 |
| 2017/0050711 A1 | 2/2017 | Kerr | | |

FOREIGN PATENT DOCUMENTS

| | | |
|---|---|---|
| RU | 2209647 C2 | 8/2003 |
| RU | 2388506 C1 | 5/2010 |
| RU | 133742 U1 | 10/2013 |
| RU | 2562033 C2 | 9/2015 |
| RU | 2568572 C1 | 11/2015 |
| RU | 2644097 C1 | 2/2018 |
| SU | 1151194 A3 | 4/1985 |

* cited by examiner

INDIVIDUAL SELF-CONTAINED BREATHING APPARATUS OF CLOSED CYCLE FOR UNDERWATER SUBMERGENCE

BACKGROUND OF THE INVENTION

1. Field of the Invention

The invention relates to self-contained breathing apparatus of closed cycle designed to protect the respiratory system when submerged under water.

2. Description of the Prior Art

Known are various designs of self-contained breathing apparatuses. Thus, the document CN206107521 discloses a semi-closed breathing apparatus, oxygen generator is linked together with a carbon dioxide absorption jar upper portion. The document U.S. Pat. No. 5,036,841 discloses a closed circuit breathing apparatus including, inter alia, a breathing reservoir, a carbon dioxide absorber and a compressed breathing gas source comprising oxygen of about 20% by volume. The document RU 2562033 discloses a breathing apparatus comprising a front part, inhalation and exhalation valves, a cartridge with a regenerative product, a breathing bag, a filter cartridge, a device for controlling the operation of the apparatus, characterized in that the filter cartridge connected to the external environment through a backflow valve contains a catalyst for the deep oxidation of harmful gas impurities and is also connected to a breathing bag, from one side, and an exhaled mixture discharge valve, from the other side, through an automatic device for controlling the operation of the apparatus.

However, they all have the following disadvantages:
- semi-closed apparatuses, i.e. include the removal of carbon dioxide formed during breathing;
- apparatuses of an alternate design demand supplying oxygen or oxygen-nitrogen breathing mixture;
- have large dimensions and weight;
- difficult to manufacture, require assembly and disassembly during storage and transportation, because they are not monoblock apparatus;
- upon availability of an oxygen cylinder, such an apparatus being dangerous due to the possibility of ignition of certain materials when in contact with oxygen under pressure.

Thus, it is an object of the present invention to provide an individual self-contained breathing apparatus of closed cycle that is safe, lightweight, simple to use, and does not require assembly prior to diving.

SUMMARY OF THE INVENTION

An individual self-contained breathing apparats of closed cycle for underwater submergence according to the present invention comprises:
- an air system, including a compensatory cylinder with compressed gas, a reducer and a manometer;
- a gas analyzing system, including sensors for determine the partial pressure of oxygen and carbon dioxide, the sensors are embedded between reactors with cartridges with an oxygen regenerating agent and a breathing bag;
- a regenerative device including the reactors with the cartridges with an oxygen regenerating agent;
- a breathing circuit including a face mask, a space under the face mask, a breathing bag, a valve for releasing pressure in the breathing circuit;
- connecting air ducts for connecting the breathing circuit to the regenerative system and the air system.

In one embodiment, the individual self-contained breathing apparatus of closed cycle includes the amount of the reactors with the cartridge with the oxygen regenerating agent is from 1 to 6. In yet another embodiment, the individual self-contained breathing apparatus include the reactors with the cartridges with the oxygen regenerating agent being an agent that chemically converts carbon dioxide gas into oxygen. In another embodiment, the individual self-contained breathing apparatus includes the cartridges with the oxygen regenerating agent, whereas the agent that chemically converts carbon dioxide gas into oxygen is chosen from a group of: $Li_2O_2$, $Na_2O_2$, $K_2O_2$, $KO_2$, $Rb_2O_2$, $Cs_2O_2$, $MgO_2$, $CaO_2$, $SrO_2$, $BaO_2$, $LiO_2$, $NaO_2$, $KO_2$, $RbO_2$, $CsO_2$, $Mg(O_2)$, $Ca(O_2)_2$, $Sr(O_2)_2$, $Ba(O_2)_2$ or superoxide ferrates $KO_2$ mixed with $CaO$.

In one additional embodiment, the individual self-contained breathing apparatus comprise the cartridges with oxygen regenerating agent that are replaceable cartridges.

In one embodiment, the individual self-contained breathing apparatus may comprise the cylinder with compressed gas may contain one of the gases being a mixture selected from the group: oxygen-nitrogen mixture, oxygen-helium mixture, oxygen-neon-helium mixture, oxygen-nitrogen-helium mixture, oxygen-neon mixture, oxygen-nitrogen neon mixture and oxygen-nitrogen-neon-helium mixture.

In another embodiment, individual self-contained breathing apparatus may additionally comprises $CO_2$ (carbon dioxide) cylinders for additional regeneration of carbon dioxide to oxygen, the cylinders connected to air ducts leading to the breathing bag, while the amount of the $CO_2$ cylinders can vary from 1 to 6.

In one embodiment, the individual self-contained breathing apparatus includes the air system, the gas analysis system, the regenerative device, the breathing circuit, and connecting pipes, all of these components being enclosed in a housing. In yet another embodiment, the individual self-contained breathing apparatus is configured such that a breathing bag occupies the free space within the housing.

In one embodiment, the individual self-contained breathing apparatus is a monoblock construction. In yet another embodiment, individual self-contained breathing apparatus is configured to be a helmet shaped or rounded. In another embodiment, the individual self-contained breathing apparatus is configured such the face mask has a full face mask configuration.

Also disclosed is the use of the individual self-contained breathing apparatus according to the invention for recreational diving, technical diving, professional diving, or rescue purposes.

DETAILED DESCRIPTION OF THE INVENTION

Figure 1:
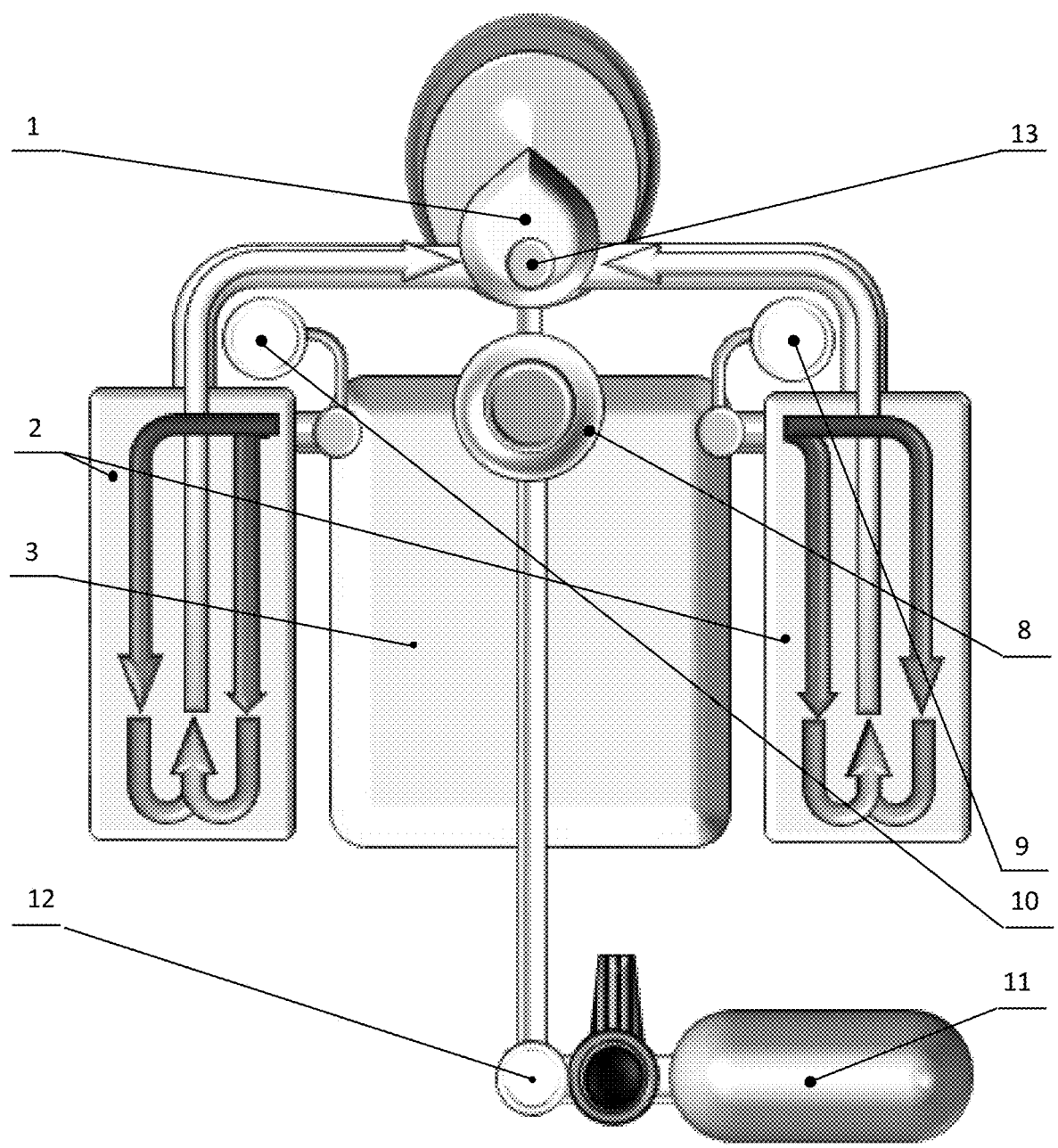
FIG. 1 schematically illustrates an individual self-contained breathing apparatus of closed cycle for underwater submersion comprising
1—a breathing mask
2—a reactor with a cartridge
3—a breathing bag
8—a reducer of the compensatory cylinder with gas
9—an $O_2$ analyzer
10—a $CO_2$ analyzer
11—a compensatory cylinder with gas 12—a manometer
13—valve for releasing pressure FIG. 2 schematically illustrates an individual self-contained breathing apparatus of closed cycle for underwater submersion comprising
1—a breathing mask
2—a reactor with cartridge
3—a breathing bag
4—a connecting hub for $CO_2$ cylinder
5—a $CO_2$ supply button
6—a $CO_2$
7—a $CO_2$ cylinder
8—a reducer of the compensatory cylinder with gas
9—an $O_2$ analyzer
10—a $CO_2$ analyzer
11—a compensatory cylinder with gas
12—a manometer
13—valve for releasing pressure
Figure 2:
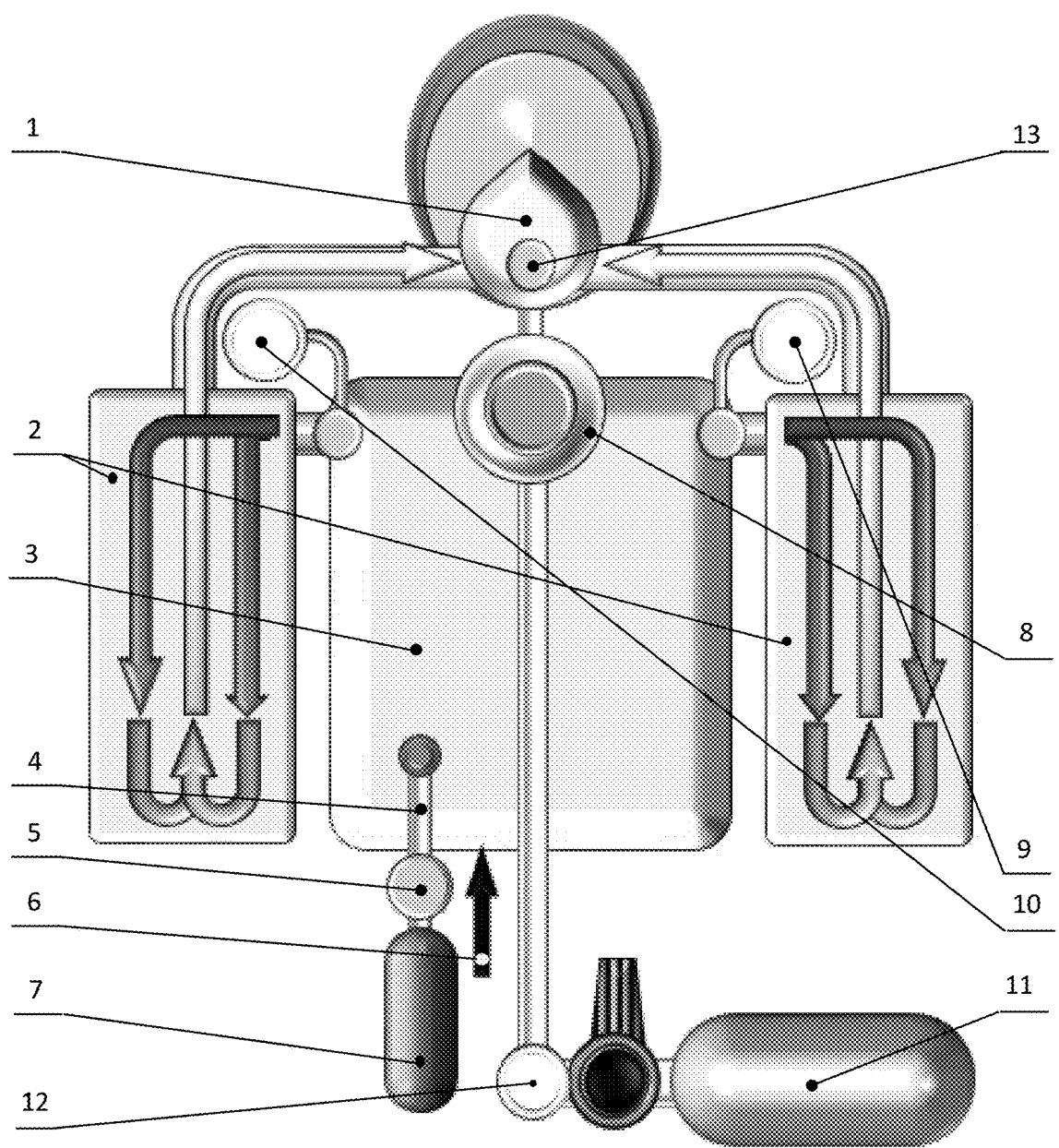

An individual self-contained breathing apparatus of closed cycle is proposed, including
an air system, including a compensatory cylinder with compressed gas, a reducer and a manometer;
a gas analyzing system, including sensors for determine the partial pressure of oxygen and carbon dioxide, the sensors are embedded between the reactors comprising cartridges with an oxygen regenerating agent and a breathing bag;
a regenerative device including reactors with cartridges with oxygen regenerating agent;
a breathing circuit including a face mask, a space under the face mask, a breathing bag, a valve for releasing pressure in the breathing circuit;
connecting air ducts for connecting the breathing circuit to the regenerative system and the air system.

The air system includes a compensatory cylinder with compressed gas, a reducer and a manometer. The cylinder with compressed gas represents a reservoir of variable suitable volume sufficient to compensate the pressure the in the breathing circuit and to be placed inside the apparatus. The compressed gas may contain one of the gases being a mixture selected from the group: oxygen-nitrogen mixture, oxygen-helium mixture, oxygen-neon-helium mixture, oxygen-nitrogen-helium mixture, oxygen-neon mixture, oxygen-nitrogen neon mixture and oxygen-nitrogen-neon-helium mixture. This cylinder is designed to add breathing mixture to the system while pressure compensating in the apparatus. When diving, an increase in external pressure occurs which leads to a decrease in the volume of the breathing circuit. To maintain a constant volume of the breathing circuit, the pressure in it must be equal to the ambient pressure, which is achieved by including a cylinder with compressed breathing mixture in the components of the apparatus. In this case, the volume of the cylinder can be 0.1-1 liter. Also, the design of the apparatus can include two compensatory cylinders with compressed gas. If there are two compensatory cylinders in the apparatus, they can be filled with different breathing mixtures. In this case, one of the cylinders can be filled with hydrogen for supply to the breathing circuit, the oxygen content in the breathing mixture is less than 5%, and the second cylinder can be filled with helium, neon, neon-helium mixture or the above mentioned breathing mixture. This usually applied in case of extended deep diving.

The face mask is intended for convenience use and can be configured as a full face mask. The full face mask is configured to fit completely over the face and obturate along the outline of the face.

The apparatus according to the invention also includes a gas analysis system. This system is designed to monitor the oxygen and carbon dioxide content in the breathing circuit. The gas analysis system includes sensors that determine the oxygen and carbon dioxide partial pressure. The sensors are positioned between the reactors with cartridges having oxygen regenerating agent and the breathing bag. This provides a correct control of the carbon dioxide and oxygen content in the breathing circuit. The sensors are either electrochemical or optical sensors. Additionally, the gas analysis system may contain sensors that determine the partial pressure of gases coming from the breathing mixture, in particular hydrogen, helium and neon.

The apparatus also includes a regenerative device, including reactors with cartridges with oxygen regenerating agent. This device is intended to regenerate exhaled carbon dioxide into oxygen. The cartridges are so positioned that the exhaled carbon dioxide enters the regenerative device, where it is converted into oxygen, which further enters the breathing bag. When inhaling, a carbon dioxide free and oxygen enriched breathing mixture enters the human lungs. This mixture can be supplemented with breathing gas from a compensatory breathing cylinder. Thus, the apparatus according to the invention is a closed cycle apparatus, without any additional air supply, oxygen or other gas or a mixture thereof required for breathing.

The apparatus has a breathing circuit including a face mask, a space under the face mask, a breathing bag, and a valve for pressure relieving in the breathing circuit. The face mask is configured to provide sufficient space between the face of the person wearing the mask and the face mask. Also a breathing bag is included in the breathing circuit, the breathing bag represents a sealed reservoir made of a soft waterproof material, preferably a polyurethane film. The breathing bag is positioned in the space inside the body of the apparatus. It has a volume from 2 to 10 liters and is intended to hold the breathing mixture that is obtained during exhalation and after passing through the reactors.

For communicating all the components of the apparatus according to the invention, the apparatus includes connecting air ducts connecting the breathing circuit to the regenerative system and the air system. These air ducts represents tubes or hoses with connector hub entering or exiting the apparatus components. Tubes or hoses are usually made of flexible elastic waterproof material. In general, the system has two air ducts connecting the face mask to the regenerative system, and two air ducts connecting the regenerative system to the breathing bag and gas analysis system. In this case, the air ducts can be located symmetrically or asymmetrically in the system.

The apparatus can additionally have sensors, air ducts and other components or parts that do not affect the general principle of the device operation.

The apparatus is usually in the shape of a helmet or a rounded shape. This provides an optimal volume of the breathing bag as well as an improvement in hydrodynamics during diving.

The total volume of the apparatus varies from 5 to 15 liters. The total weight of the apparatus can be from 3 to 15 kg. The apparatus can be used for diving to a depth of 200 meters. The volume of the reactors ranges from 0.25 to 0.8 liters, and the volume of the regenerating agent used in them being from 0.2 to 0.75 liters, with a maximum mass of the regenerating agent being up to 3 kg. The total number of reactors with regenerating agent varies from 1 to 6. The apparatus can be used for recreational diving, technical diving, professional diving or for rescue purposes. Whereas, the diving time depending on the number of regenerative cartridges and diving conditions varies from 1 to 6 hours.

Possible apparatus embodiment are shown in the Figures with only the basic principle of operation illustrated. The scope of this invention is not limited to the Figures and descriptions.

Example 1

The utilized apparatus is shown in FIG. 1. This apparatus was used for diving to a depth of 20 m. The diver was under water for 40 minutes without experiencing any side effects and discomfort. The following advantages were mentioned: ease and convenient use, no additional devices needed except for a helmet, as advantages of this apparatus over other diving apparatuses.

The invention claimed is:

1. An individual self-contained breathing apparatus of closed cycle for underwater submergence, comprising:
    an air system, including a compensatory cylinder with compressed gas, a reducer and a manometer;
    a regenerative device including reactors with cartridges with an oxygen regenerating agent, the oxygen regenerating agent being an agent that chemically converts carbon dioxide gas into oxygen;
    a gas analyzing system, including sensors for determine the partial pressure of oxygen and carbon dioxide, the sensors are embedded between the reactors with cartridges with an oxygen regenerating agent and a breathing bag;
    a breathing circuit including a face mask, a space under the face mask, the breathing bag, a valve for releasing pressure in the breathing circuit;
    connecting air ducts for connecting the breathing circuit to the regenerative device and the air system; and
    carbon dioxide cylinders for additional regeneration of carbon dioxide to oxygen, the carbon dioxide cylinders connected to air ducts leading to the breathing bag.

2. The individual self-contained breathing apparatus according to claim 1, wherein the total number of the reactors with the cartridges with the oxygen regenerating agent varies from 1 to 6.

3. The individual self-contained breathing apparatus according to claim 1, wherein the cartridges with the oxygen regenerating agent comprise as an agent that chemically converts carbon dioxide gas into oxygen, the agent is chosen from a group of: $Li_2O_2$, $Na_2O_2$, $K_2O_2$, $KO_2$, $Rb_2O_2$, $Cs_2O_2$, $MgO_2$, $CaO_2$, $SrO_2$, $BaO_2$, $LiO_2$, $NaO_2$, $KO_2$, $RbO_2$, $CsO_2$, $Mg(O_2)$, $Ca(O_2)_2$, $Sr(O_2)_2$, $Ba(O_2)_2$ and superoxide ferrates $KO_2$ mixed with CaO.

4. The individual self-contained breathing apparatus according to claim 1, wherein the cartridges with oxygen regenerating agent are replaceable cartridges.

5. The individual self-contained breathing apparatus according to claim 1, wherein the cylinder with compressed gas contains one of the gases being a mixture selected from the group: oxygen-nitrogen mixture, oxygen-helium mixture, oxygen-neon-helium mixture, oxygen-nitrogen-helium mixture, oxygen-neon mixture, oxygen-nitrogen neon mixture and oxygen-nitrogen-neon-helium mixture.

6. The individual self-contained breathing apparatus according to claim 1, wherein the amount of the carbon dioxide cylinders varies from 1 to 6.

7. The individual self-contained breathing apparatus according to claim 1, wherein the air system, the gas analyzing system, the regenerative device, the breathing circuit, the connecting air ducts being enclosed in a housing.

8. The individual self-contained breathing apparatus according to claim 7, wherein the breathing bag occupies a free space inside the housing.

9. The individual self-contained breathing apparatus according to claim 7, wherein the housing is configured to be a helmet shaped or rounded.

10. The individual self-contained breathing apparatus according to claim 1, wherein the face mask has a full face mask configuration.

11. A method of using the apparatus according to claim 1 for recreational diving, technical diving, professional diving or rescue purposes, comprising fitting the face mask over a face of an individual in need thereof and obturating along an outline of the face.

* * * * *